(12) United States Patent
Nakajima et al.

(10) Patent No.: US 7,654,990 B2
(45) Date of Patent: Feb. 2, 2010

(54) DISPOSABLE DIAPER

(75) Inventors: Kaiyo Nakajima, Kagawa-ken (JP);
Hironao Minato, Kagawa-ken (JP);
Toshimitsu Baba, Kagawa-ken (JP);
Naoko Takada, Kagawa-ken (JP); Kaori Feruya, Kagawa-ken (JP)

(73) Assignee: Uni-Charm Corporation, Shikokuchuo-Shi, Ehime-Ken (JP)

( * ) Notice: Subject to any disclaimer, the term of this patent is extended or adjusted under 35 U.S.C. 154(b) by 359 days.

(21) Appl. No.: 11/533,516

(22) Filed: Sep. 20, 2006

(65) Prior Publication Data
US 2007/0106240 A1    May 10, 2007

(30) Foreign Application Priority Data
Nov. 4, 2005    (JP)    ............................. 2005-321609

(51) Int. Cl.
*A61F 13/15*    (2006.01)
*A61F 13/20*    (2006.01)

(52) U.S. Cl. .......................... 604/385.101; 604/385.27; 604/385.19

(58) Field of Classification Search .......... 604/385.101, 604/385.01, 385.08, 385.19, 385.14
See application file for complete search history.

(56) References Cited

U.S. PATENT DOCUMENTS

| | | | |
|---|---|---|---|
| 5,520,674 A | 5/1996 | Lavon et al. | |
| 5,540,671 A | 7/1996 | Dreier | |
| 6,017,336 A | * 1/2000 | Sauer | 604/385.01 |
| 6,210,387 B1 | 4/2001 | Rudberg et al. | |
| 6,508,798 B1 | 1/2003 | Widlund et al. | |

FOREIGN PATENT DOCUMENTS

JP    2003135522    5/2003

* cited by examiner

*Primary Examiner*—Michele Kidwell
(74) *Attorney, Agent, or Firm*—Lowe Hauptman Ham & Berner

(57) ABSTRACT

A disposable diaper improved so that the wearer's skin can be reliably protected from being soiled with feces. A chassis constituting the diaper includes a spacer sheet attached to an inner sheet of the chassis. The spacer sheet has a front end zone and a rear end zone fixed to the inner sheet and an intermediate zone left free from the inner sheet. The intermediate zone is formed with an opening shaped so as to describe a circular arc which is convex forward. Along the opposite side edges of the opening, the spacer sheet is provided with elastic members extending in the length direction of the diaper and attached thereto in a stretched state in the direction. These elastic members extend forward with respect to the diaper along the peripheral edge of the opening so as to get close to a center line bisecting a width of the diaper.

17 Claims, 11 Drawing Sheets

DISPOSABLE DIAPER

BACKGROUND OF THE INVENTION

The present invention relates generally to a disposable diaper and particularly to a disposable diaper improved so as to protect the wearer against soil with feces.

One example of the disposable diaper is disclosed in Published Japanese Translation of PCT International Publication for Patent Application No. 1997-506528 (Reference 1). In this known diaper, a topsheet laid so as to come close to the wearer's skin and formed with an opening defined by a pair of opposite side edges extending in parallel to each other and these side edges are provided with elastic members which are gradually spaced from each other as these elastic members extend from an anterior portion toward a posterior portion of the opening. In the known diaper, the elastic members extending in this manner function to space the opposite side edges from each other and thereby to assure that the diaper put on the wearer can maintain a predetermined width of the opening.

Another example of the disposable diaper is also disclosed in Japanese Unexamined Patent Application Publication No. 2002-11044 (Reference 2). This diaper is particularly provided above the topsheet with a skin-contact sheet serving to protect the wearer's hip from soil with feces. The skin-contact sheet has longitudinally opposite ends bonded to the topsheet or the backsheet and is formed in its crotch region with an opening surrounded by an elastic member bonded in its stretched state to the skin-contact sheet. This diaper is put on the wearer's body with the opening overlapping the wearer's anus.

In the diaper disclosed in Reference 1, the topsheet has its front edge as well as its rear edge fixed to the diaper chassis and inevitably comes in direct contact with the buttocks and the external genital of the wearer. Such topsheet is necessarily hydrophilic and liquid-pervious since the topsheet must allow urine to permeate this topsheet. The topsheet wet with urine continuously in contact with the wearer's skin may cause diaper rash. In addition, if such liquid-pervious topsheet is loaded with the wearer's body weight as the wearer sits down or lies down, it is likely that feces staying below the topsheet may flow backs and soil the wearer's external genital and the vicinity thereof. Furthermore, in the diaper disclosed in Reference 1, the opening is formed at a long distance from the regions in which the topsheet is fixed. Consequentially, it is required to keep the elastic members in tight contact with the wearer's skin and thereby to alleviate deformation of the opening in view of the fact that the opening is formed in the crotch region which is apt to be deformed as the legs of the wearer move. However, the elastic members continuously kept in contact with the wearer's skin too tightly may cause diaper eczema. The elastic members gradually spaced from each other as these elastic members extend from an anterior portion toward a posterior portion of the opening may preferably assume that the opening also presents the corresponding shape. An appropriate transverse dimension of the opening in the vicinity of the anus is usually in a range of 3 to 6 cm to receive feces. However, the transverse dimension of the opening shaped so as to be gradually enlarged as it gets nearer to the rear end of the diaper may exceeds such appropriate range and make it difficult to protect the wearer's skin from soil with feces.

In the diaper disclosed in Reference 2, the elastic member is provided so as to surround the opening and thereby the skin-contactable sheet can be kept in close contact with the wearer's skin in front of the opening as well as behind the opening. However, similarly to the diaper disclosed in Reference 1, the skin-contactable sheet is bonded to the topsheet or the backsheet at the longitudinally opposite ends of the diaper and consequentially the crotch region of the diaper is repetitively compressed and decompressed depending on movement of the wearer's legs. In response to such repeated compression and decompression, the opening is repetitively deformed until the opening is out of alignment with the anus and feces is not received by the opening but soils the wearer's skin. Furthermore, the skin-contactable sheet is bonded to elastic members of front and rear waist regions laid along the longitudinally opposite ends of the diaper, respectively, and the opening may be deformed as a stretch ratio changes depending on the individual wearer's waist dimension.

SUMMARY OF THE INVENTION

An object of the present invention is to solve the above-mentioned problems of the conventional disposable diaper.

According to the present invention, there is provided a disposable diaper comprising a chassis and an absorbent. The chassis has a length direction, a width direction orthogonal to the length direction, front and rear sides, a front waist region defined on the front side, a rear waist region defined on the rear side and a crotch region interposed between these two waist regions. These regions respectively comprise an inner sheet adapted to come in contact with a wearer's skin and an outer sheet lying on a side opposed to the inner sheet and adapted to come in contact with an undergarment of the wearer. The absorbent is bonded between the inner and outer sheets.

The chassis is provided above the inner sheet with a spacer sheet adapted to prevent feces discharged onto the inner sheet from coming in contact with the wearer's skin. The spacer sheet has a front end zone extending aside toward the front side, a rear end zone extending aside toward the rear side and an intermediate zone extending between the front and rear end zones as viewed in the length direction. Each of these zones have opposite side edges extending in the length direction in parallel to each other. The front and rear zones are at least partially fixed to the inner sheet while at least a middle spot of the intermediate zone as viewed in the width direction is left free from the inner sheet. The intermediate zone is formed with an opening describing a circular arc which is convex toward the front side and adapted to guide the feces discharged from anus of the wearer therethrough toward the inner sheet, provided that the intermediate zone is put in contact with a vicinity of the anus. Elastic members extending in the length direction are attached in a stretched state to the spacer sheet in a vicinity of side edges of the opening as viewed in the width direction, and the elastic members provided in the vicinity of the side edges extend toward the front side along a peripheral edge of the opening so as to get close to a center line bisecting a width of the diaper.

According to one preferred embodiment of the present invention, the elastic members on the diaper held in a flatly developed state extend in the length direction substantially in parallel to each other in the vicinity of the side edges of the opening.

According to another preferred embodiment of the present invention, the elastic members provided in the vicinity of the side edges extend toward the front side so as to get close to the center line and further extend to intersect with each other on the center line or so as to get close to the center line and further extend toward the front side so as to be spaced from each other.

According to still another embodiment of the present invention, the elastic members, in a slackened state, extend toward the front side along the side edges and then extend further forward substantially linearly toward the center line.

According to yet another preferred embodiment of the present invention, the elastic members provided in the vicinity of the side edges extend toward the front side so as to intersect with each other on the center line and further extend forward to the front end zone of the spacer sheet fixed to the inner sheet.

According to further another preferred embodiment of the present invention, the rear waist region of the chassis is provided along both sides thereof opposed to each other in the width direction with elastically stretchable/contractible regions, respectively, between which the rear end zone of the spacer sheet is laid and fixed to a region of the inner sheet overlying the absorbent.

According to an additional preferred embodiment of the present invention, the diaper is of a pants type in which the front and rear waist regions in the chassis are bonded together along opposite side edges thereof.

According to further additional preferred embodiment of the present invention, the elastic members stretchably/contractibly extend in the width direction in the crotch region of the diaper.

In the disposable diaper according to the present invention, the inner sheet of the chassis is provided with the spacer sheet having the front and rear end zones fixed to the inner sheet and the intermediate zone formed with the opening adapted to receive feces. In the vicinity of the opposite side edges of this opening, the elastic members extending forward in the length direction are attached in a stretched state to the spacer sheet. These elastic members extending forward gradually get close to the center line so as to cooperate with each other and thereby to describe the circular arc which is convex forward. When the diaper is put on the wearer's body so that the opening overlies the anus and consequently the width of the crotch region is reduced, the respective elastic members having described the circular arc heretofore are linearly deformed under contractile force thereof into a V-shape about the center line. Correspondingly, the front segment of the opening's peripheral edge also is deformed into a V-shape and smoothly received by the posterior rugae. Within such posterior rugae, the opening's peripheral edge is held in close contact with the wearer's skin on both sides of the anus. Consequentially, feces discharged from the anus can be reliably guided through the opening held within the posterior rugae into the space defined between the spacer sheet and the inner sheet of the chassis. The presence of the spacer sheet effectively eliminates the anxiety that feces having been guided into the space might come in contact with the wearer's skin around the anus.

According to the present invention wherein the elastic members provided in the vicinity of the side edges of the opening extend in the length direction substantially in parallel to each other, it is ensured that the spacer sheet can be evenly held in close contact with the wearer's skin on both sides of the anus and feces can be smoothly guided through the opening.

According to the present invention wherein the elastic members intersect with each other on the center line or get closest to each other in the vicinity of the center line, the elastic members having described the circular arc heretofore are deformed into the V-shape as the width of the crotch region is reduced so that the spot corresponding to the apex of the V-shape can be kept in contact with the wearer's skin in front of the anus.

According to the present invention wherein the elastic members, in a slackened state, extend from the both sides of the opening forward substantially linearly toward the center line, the spacer sheet adequately covers the wearer's skin in front of the anus and thereby substantially protects the external genital and the skin in the vicinity thereof from soil with feces having been guided through the opening into the space.

According to the present invention wherein the elastic members extending in the length direction intersect with each other on the center line and further extend forward to the front end zone of the spacer sheet, a volume of the space can be enlarged by spacing the spacer sheet, in the vicinity of its front end zone, from the inner surface of the chassis.

According to the present invention wherein the rear end zone of the spacer sheet is fixed to the inner sheet its region overlying the absorbent, stretching and contraction, if occur, of the elastic zones defined in the rear end zone of the spacer sheet will hardly affect the rear end zone of the spacer sheet and hardly reduce the width of the opening in the rear end zone of the spacer sheet.

According to the present invention wherein the diaper is of a pants-type in which the front and rear waist regions in the chassis are bonded together along opposite side edges thereof, relative positions of the front and rear waist regions do not depend on the manner in which the diaper is put on the wearer's body and therefore the opening of the spacer sheet can be easily aligned with the anus when the used diaper is exchanged with a fresh one.

According to the present invention wherein the elastic members contractibly extend in the width direction in the crotch region of the diaper, contraction of the elastic members automatically reduce the width of the crotch region and therefore the elastic members initially attached to the spacer sheet so as to describe the circular arc are readily deformed so as to extend linearly.

DETAILED DESCRIPTION OF THE PREFERRED EMBODIMENTS

Details of a disposable diaper according to the present invention will be more fully understood from the description given hereunder with reference to accompanying drawings.

Figure 1:
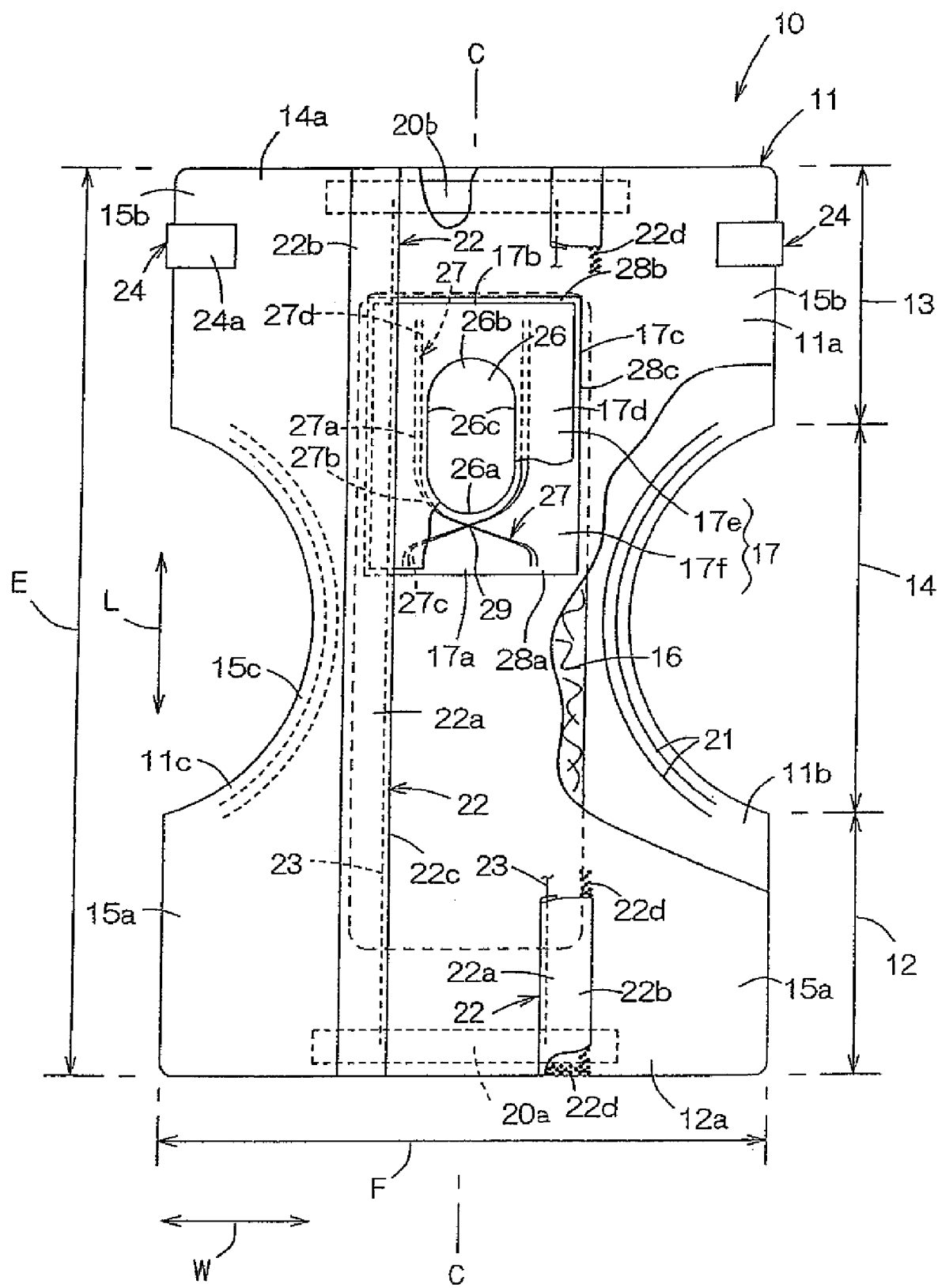
FIG. 1 is a partially cutaway plan view depicting a diaper.
Figure 2:
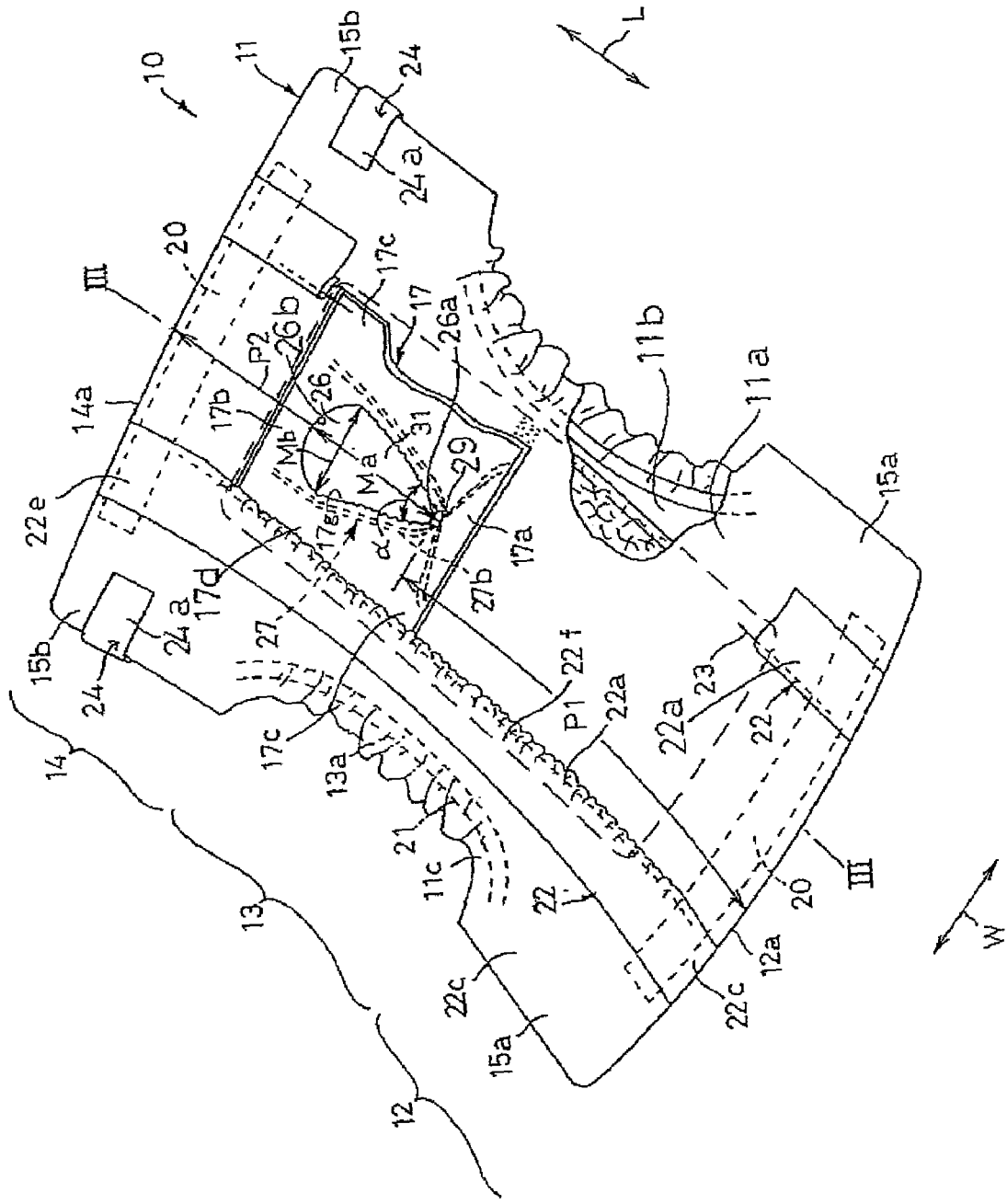
FIG. 2 is a partially cutaway perspective view depicting the diaper in its state left free.
Figure 3:
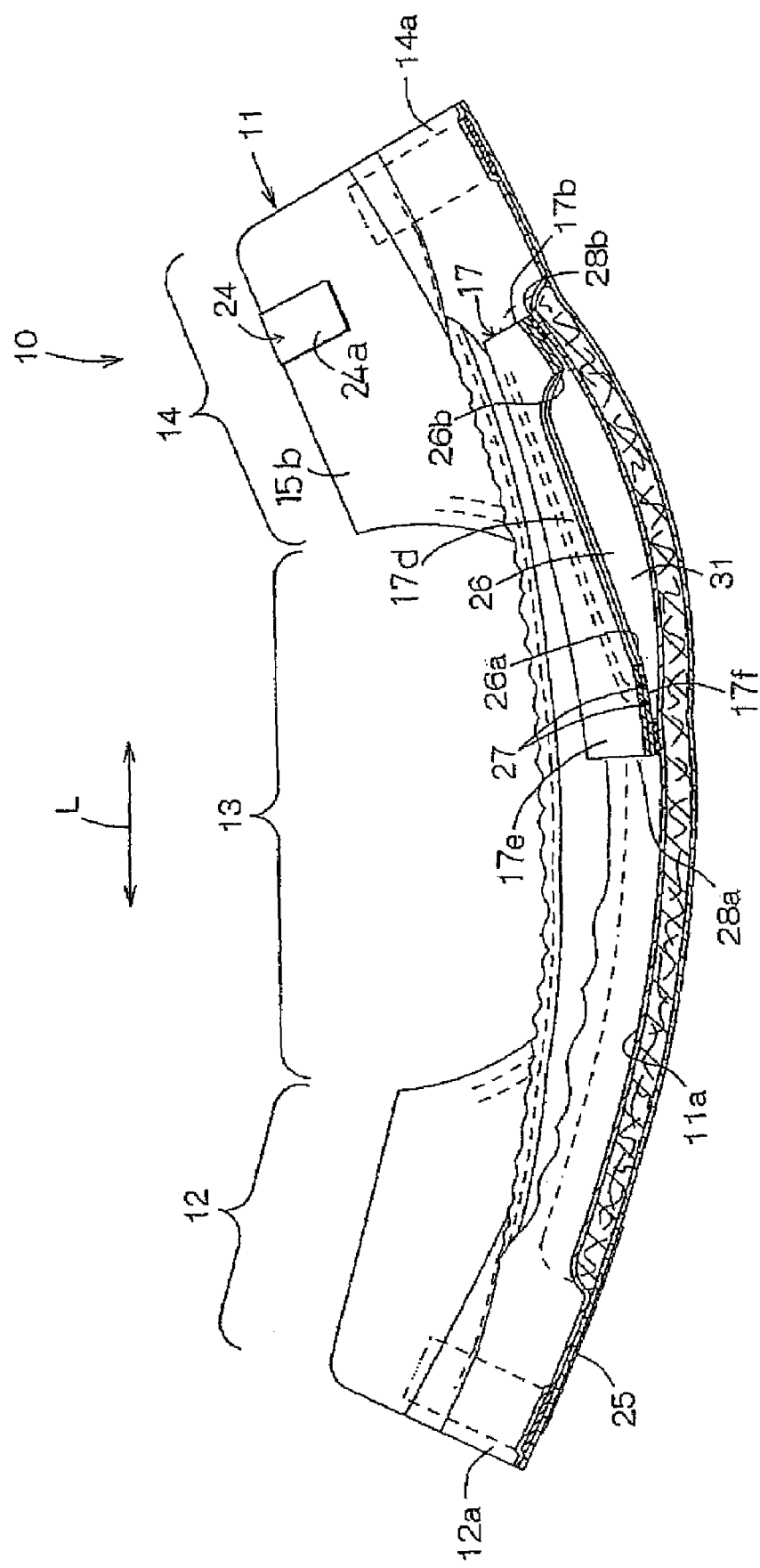
FIG. 3 is a sectional view taken along the line III-III in FIG. 2.

FIG. 1 is a partially cutaway plan view depicting an open-type disposable diaper 10 in its flatly developed state, FIG. 2 is a partially cutaway perspective view depicting the diaper 10 in its state left free and FIG. 3 is a sectional view taken along the line III-III in FIG. 2.

Referring to FIG. 1, a diaper 10 has a length direction L and a width direction W orthogonal to each other and is symmetric with each other about a center line C extending in the length direction L so as to bisect a dimension of the diaper 10 in the width direction W. The diaper 10 comprises a chassis 11 having a front waist region 12 lying on a front side as viewed in the length direction L, a rear waist region 13 lying on a rear side as viewed in the length direction L and a crotch region 14 interposed between these two waist regions 12, 13. The chassis 11 contains therein an absorbent 16 which is semi-rigid and capable of absorb bodily discharges. The chassis 11 may be referred to also as a main body.

The chassis 11 has an hourglass-like planar shape having a narrow region defined by the crotch region 14 curved inward as viewed in the width direction W and comprises a liquid-pervious inner sheet 11a defining an inner surface adapted to come in contact with the wearer and a liquid-impervious outer sheet 11b defining an outer surface opposed to the inner sheet 11a and adapted to come in contact with an undergarment of the wearer. The absorbent 16 is interposed between these two sheets 11a, 11b. The inner sheet 11a is bonded to the absorbent 16 with bonding means (not shown) such as a hot melt adhesive and a part of the inner sheet 11a extending outward beyond a peripheral edge of the absorbent 16 is bonded to the outer sheet 11b with a hot melt adhesive or sealing technique. A liquid-impervious or liquid-resistant spacer sheet 17 partially overlies the inner sheet 11a so as to cover the rear waist region 13 and a part of crotch region 14 contiguous to the rear waist region 13. The term "liquid-resistant sheet" used herein refers to a sheet being not liquid-impervious but capable of constraining any remarkable permeation of liquid that may cause undesirable leakage or exudation of body liquid. Such spacer sheet 17 has a front end zone 17a, a rear end zone 17b and an intermediate zone 17d between these opposite end zones 17a, 17b as viewed in the length direction L. These zones 17a, 17b, 17d commonly have a pair of side edges 17c extending in the length direction L generally in parallel to each other. The front end zone 17a and the rear end zone 17b are at least partially fixed to the inner sheet 11a with a hot melt adhesive or sealing technique but, in the vicinity of the side edges 17c of the respective zones 17a, 17b, 17d are fixed or not fixed to the inner sheet 11a as the case may be. A middle section as viewed in the width direction W, i.e., a section extending inside the side edges 17c of the intermediate zone 17d is left free from the inner sheet 11a so that this middle section can be spaced upward as viewed in FIG. 3 from the inner sheet 11a.

In the chassis 11, the front waist region 12 has a front end 12a and opposite side edges 15a while the rear waist region 13 has a rear end 14a and opposite side edges 15b. The crotch region 14 has opposite side edges 15c curved toward the center line C and these side edges 15c are contiguous to those side edges 15a and 15b, respectively, as shown. In the front and rear waist regions 12, 13, belt-like waist elastic members 20a, 20b are sandwiched between the inner sheet 11a and the outer sheet 11b and bonded in a stretched state to at least one of these two sheets 11a, 11b. Along the opposite side edges 15c of the crotch region 14, leg elastic members 21 each comprising a plurality of rubber threads are sandwiched between the inner sheet 11a and the outer sheet 11b and bonded in a stretched state to at least one of these two sheets 11a, 11b. The opposite side edges 15c including these leg elastic members 21 respectively form gasket cuffs in the diaper 10. In the chassis 11, elongate barrier cuffs 22 extending in the length direction L are attached to the inner sheet 11a. Each of the barrier cuffs 22 is provided separately of the inner sheet 11a and formed from a liquid-resistant, more preferably liquid-impervious sheet. The barrier cuff 22 comprises a distal portion 22a adapted to rise up on the inner sheet 11a and a proximal portion 22b bonded to the inner sheet 11a with a hot melt adhesive 22d. The distal portion 22a has an uppermost edge 22c to which a cuff elastic member 23 formed from a rubber thread extending in the length direction L is attached in a stretched state. When the diaper 10 bows with the inner surface 11a lying inside as shown in FIGS. 2 and 3, the respective distal portions 22a rise up above the inner sheet 11a as the cuff elastic members 23 contract. In this way, the distal portion 22a form leak-barriers serving to prevent body fluids from leak sideways.

In the chassis 11, the opposite side edges 15b of the rear waist region 13 are provided with a pair of tape fasteners 24 to connect the front and rear waist regions 12, 13 in a circumferential direction. Each of these tape fasteners 24 comprises a proximal section (not shown) permanently bonded to the associated side edge 15b and a fastening section 24a adapted to be developed outward from the diaper 10 as viewed in FIG. 1 and to be fastened to the front waist region 12. The outer sheet 11b in the front waist region 12 is provided with a target tape strip 25 (See FIG. 3) as a counterpart for the tape fasteners 24. Specifically, the respective fastening sections 24a of the tape fastener 24 are detachably anchored on the target tape strip 25. Means adopted by the fastening section 24a to anchor this fastening section 24a on the target tape strip 25 may be selected from the group consisting of a pressure-sensitive adhesive, a hook member constituting a so-called mechanical fastener and a loop member constituting the mechanical fastener.

The spacer sheet 17 is formed in its intermediate 17d with an oval opening 26 and in the vicinity of side edges 26c of this opening 26 which are opposite to each other as viewed in the width direction W with spacer elastic members 27 each comprising a single or plural rubber threads. These elastic members 27 are bonded in a stretched state to the spacer sheet 17 and allow the spacer sheet 17 to be spaced upward from the inner sheet 11a. As will be obviously understood from FIG. 1, these paired spacer elastic members 27 comprise lateral segments 27a linearly extending in the length direction L in the vicinity of the side edges 26c, curved segments 27b extending to the center line C on the front side of the opening 26 along arc-shaped front segment 26a constituting the peripheral edge of the opening 26 and front segments 27c extending from a cross point 29 of the curved segments 27b on the center line C close to the front end zone 17a of the spacer sheet 17. In the vicinity of the cross point 29, these spacer elastic members 27 describe an X-shape. Rear segments 27d extending rearward from the side edges 26c of the opening 26 linearly extend toward the rear end zone 17b of the spacer sheet 17 without intersecting each other.

While it is possible to form such spacer sheet 17 from a single sheet, the spacer sheet 17 is preferably formed from a pair of sheets 17e, 17f placed upon each other as shown by FIG. 1. Between these two sheets 17e, 17f, the spacer elastic members 27 are sandwiched and bonded in a stretched state to at least one of these two sheets 17e, 17f. While the front and rear end zones 17a, 17b are bonded to the inner sheet 11a preferably over the full dimensions thereof in the width direction W, it is alternatively possible to bond the front and rear end zones 17a, 17b to the inner sheet 11a only in the vicinity of the front and rear segments 27c, 27d of the spacer elastic members 27. While the separator sheet 17 is bonded in the vicinity of the side edges 17c to the inner sheet 11a preferably over the full dimension of the separator sheet 17, it is alternatively possible to bond the spacer sheet 17 along the side edges 17c thereof to the inner sheet 11a only in the intermediate zone 17d. In any case, the front and rear end zones 17a, 17b are at least partially bonded to the inner sheet 11a and, in the vicinity of spots at which those zones 17a, 17b are bonded to the inner sheet 11a, the inner sheet 11a is bonded to the absorbent 16. Therefore, the spacer sheet 17 is not readily deformed unless the absorbent 16 is deformed. Consequentially, neither the position nor the shape of the opening 26 relative to the wearer is readily deformed unless the absorbent 16 is deformed.

The term "the diaper 10 flatly developed" refers to a state in which the diaper 10 bowed as the elastic members are left contract as seen in FIGS. 2 and 3 has been pulled in the length direction L as well as in the width direction W until the gathers due to contraction of the respective elastic members have disappeared and the inner and outer sheets 11a, 11b of the chassis 11 have restored primary planar shapes thereof.

As will be seen in FIGS. 2 and 3, the waist elastic members 20, the leg elastic members 21 and cuff elastic members 23 contract as the diaper 10 is left free and the diaper 10 is gently bowed with the inner sheet 11a lying inside so that the front and rear ends 12a, 14a or these ends and the side edges 15a, 15b as well as their vicinities are risen upward. Thereupon the nonwoven fabric and the film are formed with a plurality of gathers extending across the respective elastic members. It should be noted that these gathers are partially shown in FIGS. 2 and 3. Between the front and rear end zones 17a, 17b of the spacer sheet 17, the chassis 11 is bowed so as to be convex with the outer sheet 11b lying outside while the spacer sheet 17 is spaced from the inner sheet 11a as the spacer elastic members contract so as to form a space 31 between these two sheets 17, 11. The opening 26 defines an inlet for this space 31. An apparent dimension of the chassis 11 in the width direction W is reduced as the waist elastic members 20 contract and simultaneously the side edges 17c of the spacer sheet 17 move toward the center line C and correspondingly an apparent width dimension of the spacer sheet 17 also is reduced. Thereupon the curved segments of the spacer elastic members 27 on both sides of the center line C linearly contract so as to describe together a V-shape and the arc-shaped front segment 26a also are deformed together into a V-shape formed with a plurality of gathers. During this process, the dimension of the opening 26 in the width direction W is not markedly changed in the vicinity of the rear end zone 17b of the spacer sheet 17 but significantly changed in the vicinity of the front segment 26a constituting the opening 26. A width of the crotch region 14 is further reduced and deformation of the front segment 26a into V-shape also becomes further remarkable as the diaper 10 is put on the wearer's body and the crotch region 14 is squeezed between thighs. Provided that, in such diaper 10, the spacer sheet 17 is attached to the chassis 11 with the opening 26 opposed to the wearer's anus, the opposite side edges 26c of the opening 26 will be reliably received together with the spacer elastic members 27 by the posterior rugae within which the side edges 26c will come in close contact with the wearer's skin on both sides of the anus. Consequently, feces discharged from the wearer will be smoothly received by the opening 26 fixedly located within the posterior rugae. The spacer sheet 17 is attached to the inner sheet 11 in a manner also that a region of the spacer sheet 17 defined by the X-shaped cross point of the spacer elastic members 27 and the vicinity thereof may come in contact with the wearer's skin at a position anterior to the anus and posterior to the external genital. Compared to the state shown in FIG. 1 in which the diaper 10 has been flatly developed, the opening 26 of the spacer sheet 17 in the state as has been described just above has its dimension Mb in the width direction W is gradually reduced under the contractile force of the spacer elastic members 27 toward the front segment 26a, in other words, toward the external genital. As an advantageous result, an anxiety that feces once having been received in the space 31 might flow back through the opening 26 can be substantially prevented while another anxiety that urine discharged from the external genital and flowing rearward might flow into the space 31 can be substantially prevented. Thus it is possible for the diaper 10 of FIG. 1 to facilitate feces to flow into the space 31, to prevent the wearer's external genital from soil with feces and to prevent urine and feces from being mixed together within the space 31.

In the case of the embodiment according to which the spacer sheet 17 is fixed to the inner sheet 11a fully along the front and rear end zones 17a, 17b as well as the both side edges, the space 31 fluid-communicates with the exterior only through the opening 26. While the space 31 defined in this manner is effective to decrease the likelihood that feces having been received by the space 31 might flow back and soil the wearer's skin, the spacer sheet 17 fixed to the inner sheet 11a along full length of the side edges 17c may disadvantageously limit the desired contraction of the spacer elastic members 27 and obstruct the desired deformation of the curved segments 26c of the opening 26 from the circular arc to the V-shape. To avoid this, the spacer sheet 17 may be left free from the inner sheet 11a along portions of the respective side edges 17c, for example, along the side edges 17c of the intermediate zone 17d to facilitate the desired contraction of the spacer elastic members 27. The higher a contraction percentage of the spacer elastic members 27 is, the larger a distance of the spacer sheet 17 spaced from the inner sheet 11a is, so the correspondingly deeper space 31 is formed. After received by such deep space 31, feces moving in the width direction W are effectively held back by the barrier cuffs 22 and there is no anxiety that any amount of feces might leak out from the diaper 10. The barrier cuffs 22 functioning in this manner are preferably dimensioned so that the respective cuff sections 22 may overlap the spacer sheet 17 as these barrier cuffs 22 are collapsed toward the center line C (See FIG. 1). The region of the spacer sheet 27 including the curved segments 27b is deformed so as to extend rather linearly and simultaneously formed with the gathers 17g. In such region, the gathers 17g are unfolded or refolded depending on movement of the wearer's skin with which this region is kept in close contact and thereby this region can be reliably kept in close contact with the wearer's skin. In this way, the spacer sheet 17 reliably keeps feces received within the space 31 away from the wearer's skin and protects the wearer's skin from soil with feces.

Assumed that the diaper 10 is left free as shown in FIGS. 2 and 3, the opening 26 preferably has a dimension as measured in the length direction L from the front segment 26a to the rear segment 26b in a range of 50 to 200 mm and the maximum dimension Mb as measured in the width direction W in a range of 30 to 100 mm. With respect to the opening deformed into the V-shape, an opening angle α defined by the front segment 26a is preferably in a range of 40 to 130°. The preferred spacer sheet 17 is attached to the inner sheet 11a in a manner that a region of the sheet 17 defined at a distance in a range of 30 to 90 mm rearward from the front segment 26a of the opening 26 may be substantially aligned with the diaper wearer's anus. A dimension Ma of the opening 26 aligned with the anus in this manner is preferably at least 20 mm larger than the distance as indicated just above. If the maximum dimension Mb is less than 30 mm and/or the opening angle α is less than 40°, the opening 26 may be closed and it may be impossible to guide feces into the space 31. On the contrary, if the maximum dimension Mb exceeds 100 mm and/or the opening angle α exceeds 130°, fitness to the skin around the anus achieved by the both side edges 26c of the opening 26 within the posterior rugae will be deteriorated and consequentially it will become to guide feces through the opening 26. If the distance from the front segment 26a to the anus is less than 30 mm, movement of the spacer sheet 17 relative to the wearer's buttocks will cause feces to run upon the spacer sheet 17 rather than to move toward the opening 26. As a result, the wearer's skin will be readily soiled with feces. On the other hand, if the distance from the front segment 26a of the opening 26 to the anus exceeds 90 mm, the wearer's external genital will be partially exposed in the opening 26 and apt to be soiled with feces.

Of the diaper 10 constructed in the manner as has been described above, the inner sheet 11a may be formed, for example, from a liquid-pervious nonwoven fabric made of thermoplastic synthetic fibers or a liquid-pervious perforated film made of a thermoplastic synthetic resin both preferably modified to become hydrophilic. The outer sheet 11b may be formed, for example, from a liquid-impervious or liquid-resistant nonwoven fabric made of hydrophobic thermoplastic synthetic fibers, a liquid-impervious or liquid-resistant film made of a thermoplastic synthetic resin or a composite sheet consisting of the above described film and the above-described nonwoven fabric laminated on the outer side of the former. An example of the liquid-resistant film comprises an air-permeable film made of a polyolefin-based synthetic resin commingled with fine particles, for example, of calcium carbonate or barium sulfate and subjected to mono- or biaxial orientation.

The absorbent 16 comprises, for example, fluff pulp fibers having water absorption properties, a mixture of fluff pulp fibers and a thermoplastic synthetic resin having no water absorption properties, a mixture of fluff pulp fibers and super-absorbent polymer particles or a mixture of fluff pulp fibers, thermoplastic synthetic fibers and super-absorbent polymer particles, in any case, wrapped with a cover sheet made of a liquid-pervious and hydrophilic tissue paper or a crepe paper or nonwoven fabric, followed by a treatment of compression. The absorbent 16 exhibits a flexural rigidity higher than those of the inner sheet 11a and the outer sheet 11b but can be easily curved as illustrated in FIGS. 2 and 3 under the effect of the respective elastic members. Such absorbent 16 may be referred to as a semi-rigid absorbent. For the case in which the absorbent 16 contains the super-absorbent polymer particles, a melt blown nonwoven fabric constituted by sufficiently fine fibers is suitable as the cover sheet. Specifically, compared to the case in which a nonwoven fabric of the other type having the same basis weight as the melt blown nonwoven fabric but relatively large fineness is used, fiber interstices are preferably kept sufficiently small to prevent the super-absorbent polymer particles swollen with absorbed urine from falling off through the fiber interstices. The shape of the absorbent 16 is not specified and may be rectangular as illustrated in FIG. 1 or hourglass-like. While the absorbent 16 having a uniform thickness is shown in FIG. 3, the absorbent 16 may have a depression in a region opposed to the opening 26 of the spacer sheet 17 or this region may be devoid of water absorptive materials (See FIG. 1). However, it is essential that the dimension of the absorbent 16 in the region opposed to the opening 26 as measured in the width direction W should be larger than the dimension of the opening 26 as measured in the width direction.

The waist elastic members 20, the leg elastic members 21, the cuff elastic members 22 and the spacer elastic members 27 may be formed from rubber threads, a flat rubber or the like made of an elastomeric material such as a natural rubber, a synthetic rubber or an urethane foam.

The barrier cuffs 22 may be formed from a liquid-impervious or liquid-resistant nonwoven fabric or a film made of a thermoplastic synthetic resin.

Figure 4:
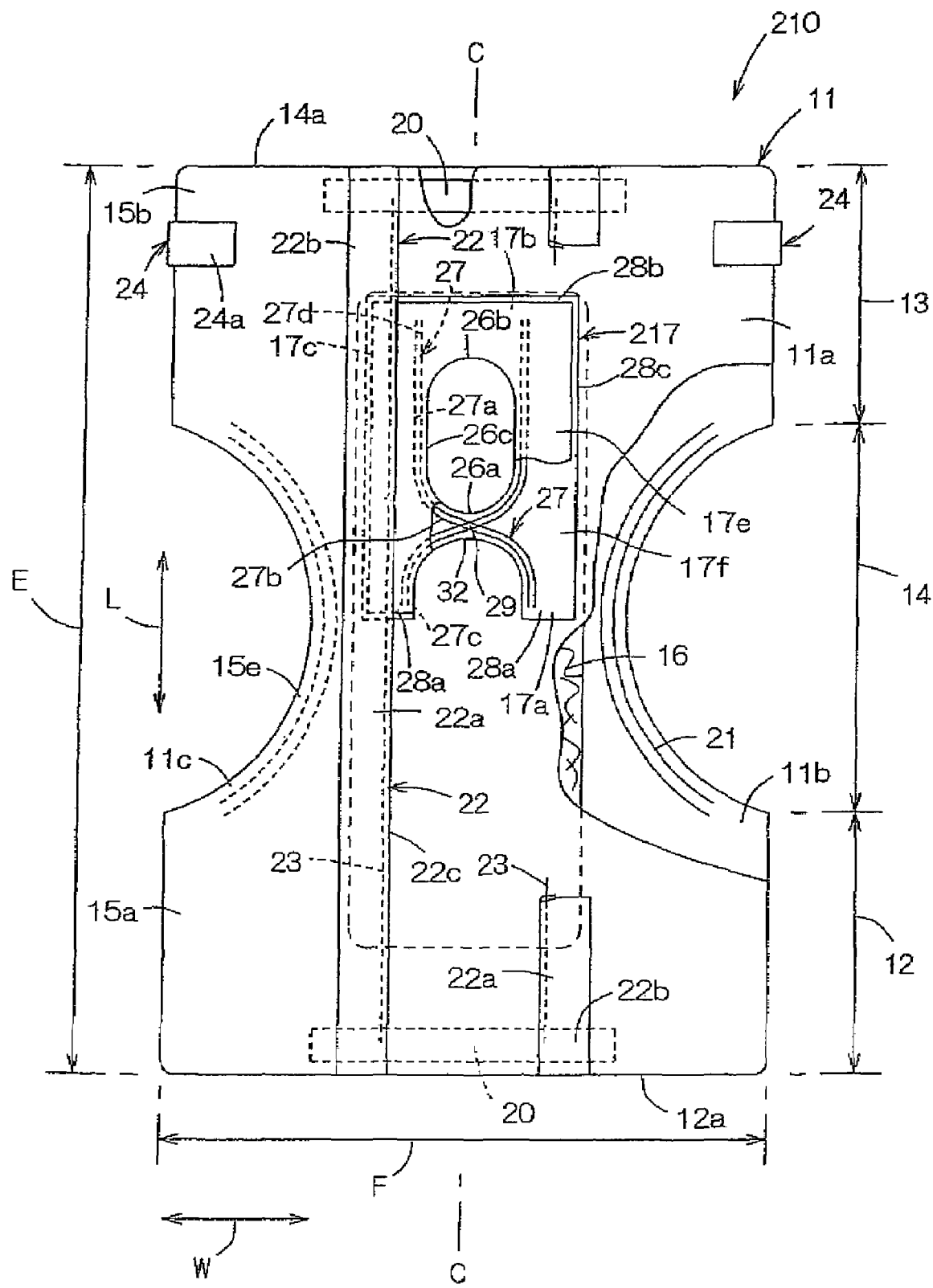
FIG. 4 is a partially cutaway plan view depicting the diaper according to one preferred embodiment of the present invention.
Figure 5:
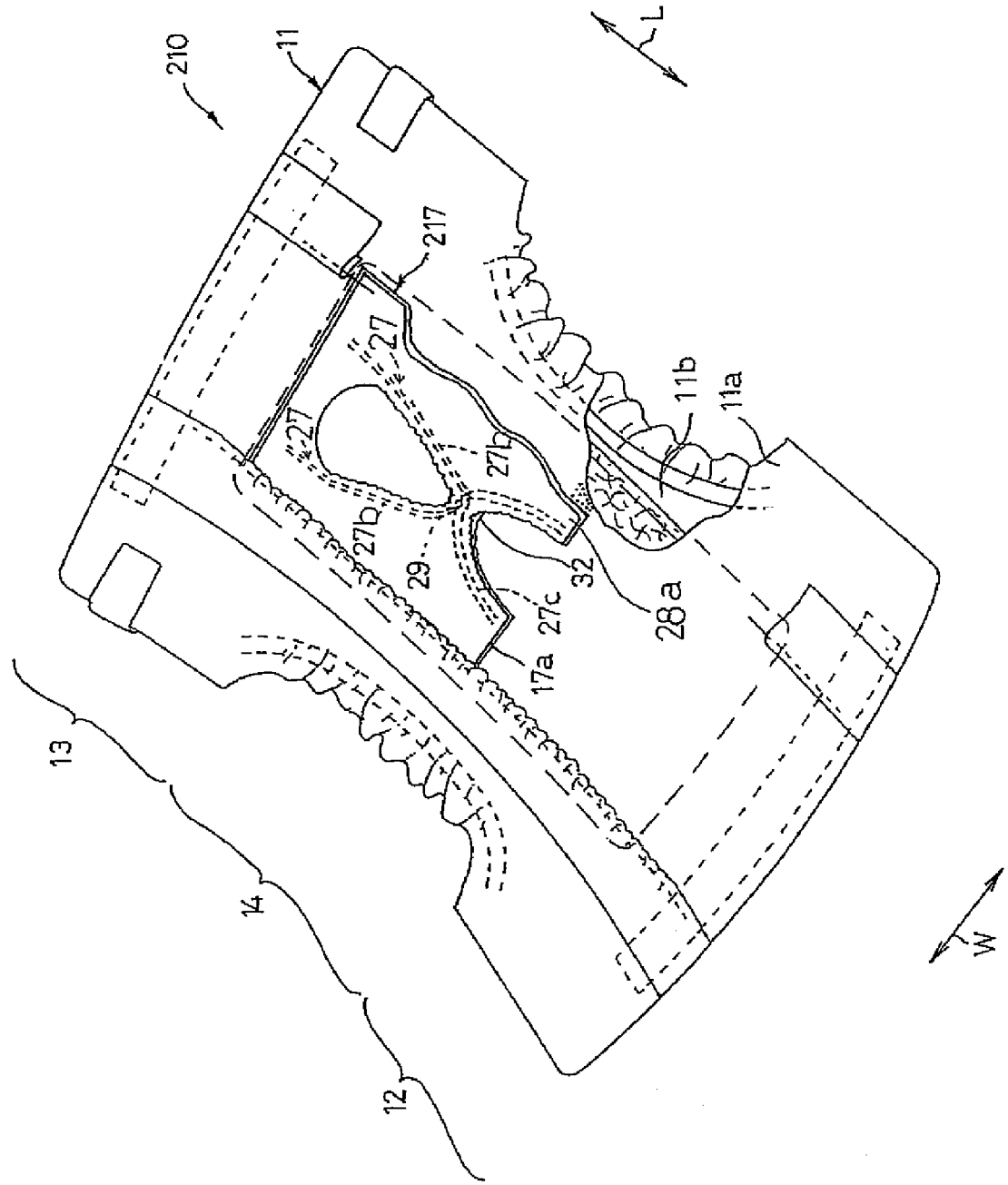
FIG. 5 is a partially cutaway perspective view depicting the diaper of FIG. 4 in its state left free.

FIGS. 4 and 5 are views similar to FIGS. 1 and 2, respectively, depicting a diaper 210 according to one preferred embodiment of the present invention. The diaper 210 is similar to the diaper 10 of FIG. 1 except that the diaper 210 has a spacer sheet 217 configured in a manner differing from the diaper 10 of FIG. 1. Referring to FIG. 4, the front end zone 17a of the spacer sheet 217 is formed in the middle of the front end zone 17a as viewed in the width direction with a substantially semicircular notch 32 and the spacer elastic members 27 are contractibly attached to the spacer sheet 217 so as to extend along the notch 32 and to intersect with each other at the cross point 29 from which these spacer elastic members 27 extend to the leftover front end zones 17a of the spacer sheet 217. Segments 28a of the front end zone 17a linearly extending in the width direction W except the notch 32 are fixed to the inner sheet 11a with an adhesive or sealing technique. The rubber threads of the respective spacer elastic members 27 extending in parallel one to another are spaced one from another substantially by regular intervals. When the diaper 210 is left free to bow under contraction of the respective elastic members, the segments 27b, 27c of the spacer elastic members 27 also contract so as to be deformed in substantially straight lines and to describe an X-shape in the vicinity of the notch 32. In the case of the spacer sheet 217 having the front end zone 17a which extends forward by a longer range than the front end zone 17a in the diaper 10 of FIG. 1, such spacer sheet 217 is preferably formed with the notch 32 and thereby the inner sheet 11a is partially exposed so that the exposed region may be effectively used for absorption of urine.

Figure 6:
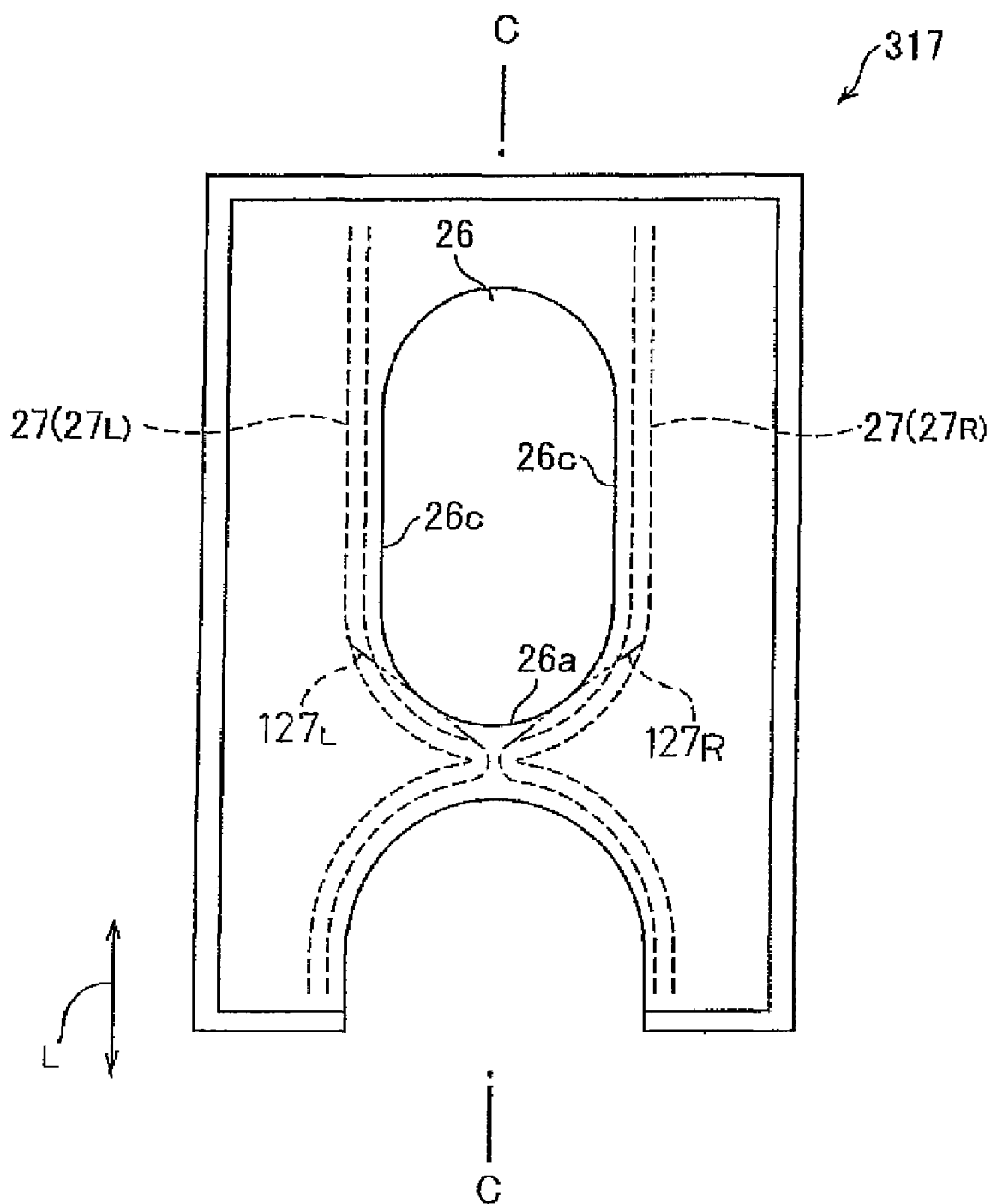
FIG. 6 is a plan view depicting one preferred embodiment of the separator sheet.

FIG. 6 is a plan view depicting one preferred embodiment of the separator sheet used for the present invention. The spacer sheet 317 illustrated herein is similar to the spacer sheet 217 in FIG. 4 as long as the shape of the sheet itself is concerned but distinguished from the spacer sheet 217 with respect to a layout of the spacer elastic members 27. Specifically, the spacer elastic members 27 comprising first and second elastic members 27L, 27R linearly extending in the length direction L on the left and right sides, respectively, of the opening 26 and then coming closest to each other in a region defined in a vicinity of the center line C without intersecting with each other. In front of this region, the elastic members 27L, 27R extend apart from each other to keep an explicit distance as is the case occurring behind the region defined in the vicinity of the center line C. With this spacer sheet 317 also, it is ensured that the first and second elastic members 27L, 27R contract so as to extend linearly as indicated by imaginary lines 127L, 127R and simultaneously the front end segment 26a of the opening 26 is deformed to describe the V-shape as the width of the diaper's crotch region is reduced, for example, when the diaper is put on the wearer's body. In this way, the first and second elastic members 27L, 27R can cooperate with each other to describe the X-shape in the vicinity of the front segment 26a.

Figure 7:
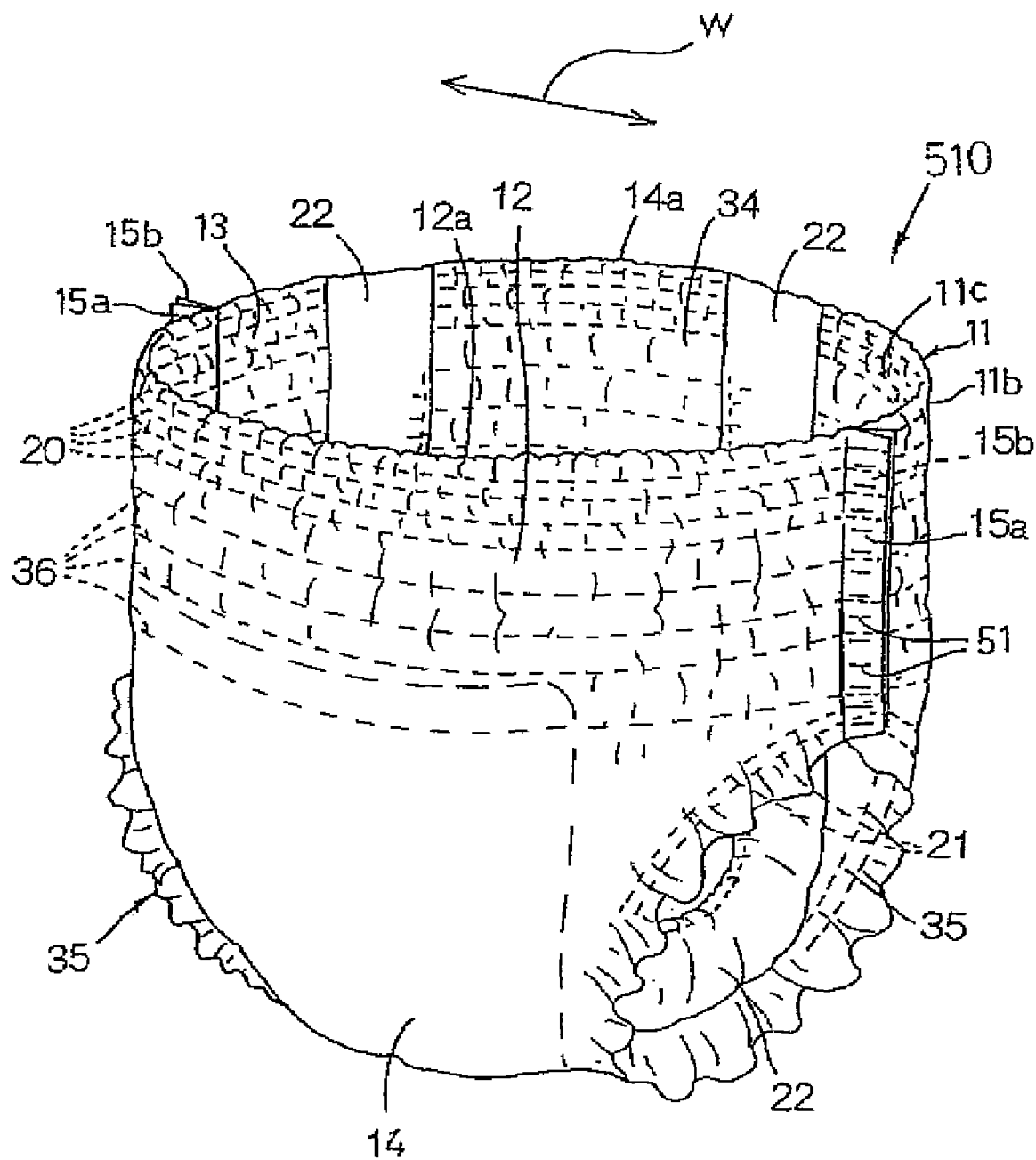
FIG. 7 is a perspective view depicting a pants-type diaper according to another preferred embodiment of the present invention.
Figure 8:
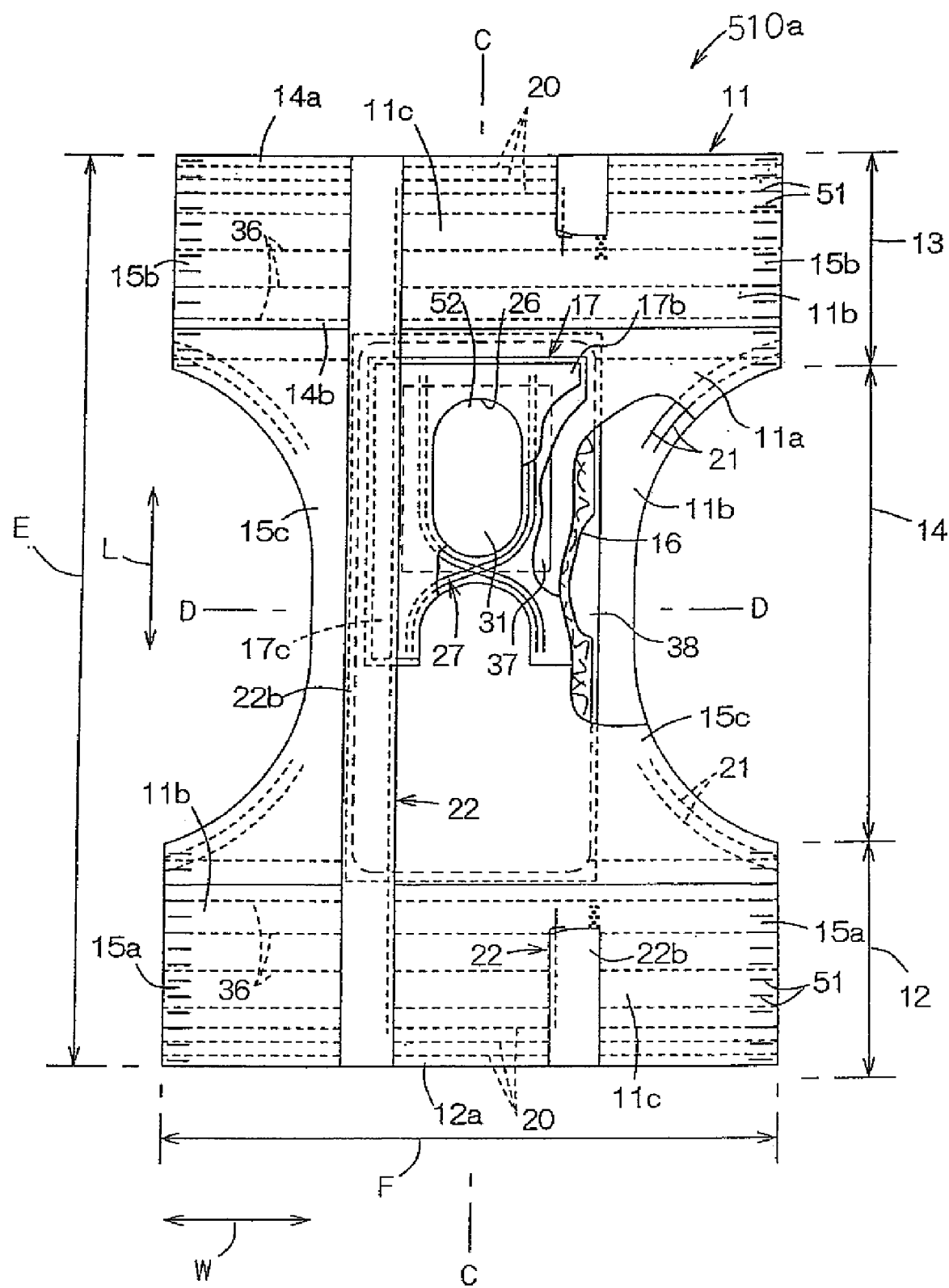
FIG. 8 is a view similar to FIG. 4, depicting the diaper of FIG. 7 in its flatly developed state.
Figure 9:
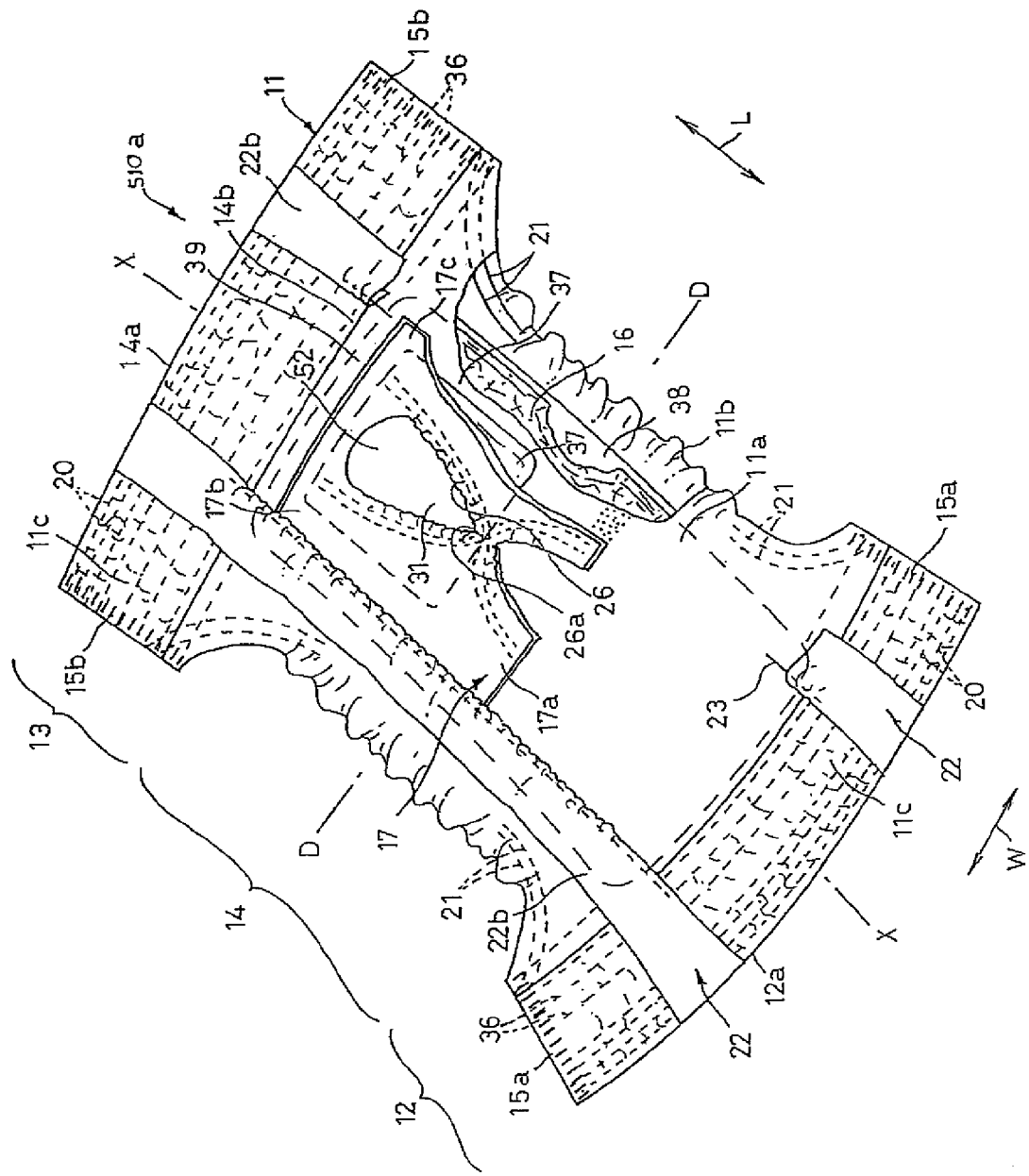
FIG. 9 is a view similar to FIG. 5, depicting the diaper of FIG. 8.
Figure 10:
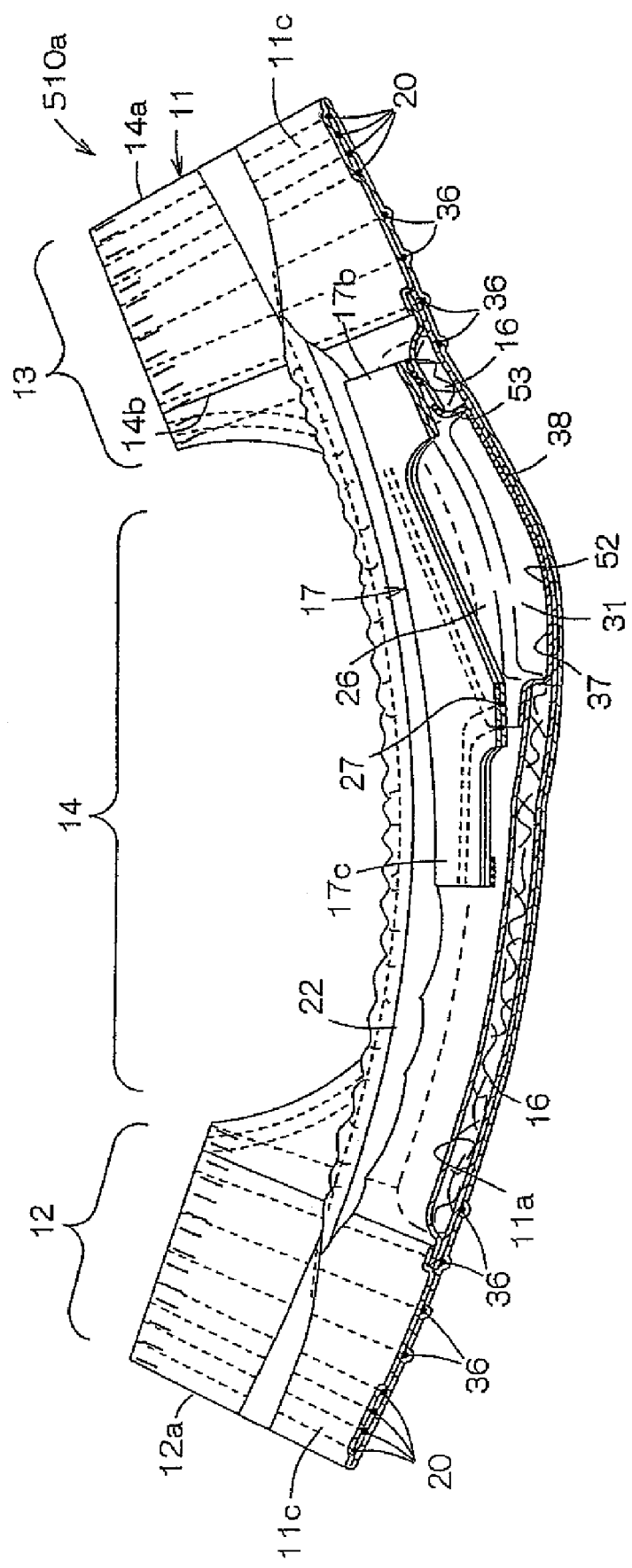
FIG. 10 is a sectional view taken along the line X-X in FIG. 9.

FIG. 7 is a perspective view depicting a pants-type diaper 510 according to another preferred embodiment of the present invention, FIG. 8 is a partially cutaway plan view depicting a diaper 510a having the front and rear waist regions 12, 13 and the crotch region 14 flatly developed similarly to FIG. 4, FIG. 9 is a partially cutaway perspective view, depicting the diaper 510a in the state left free and FIG. 10 is a sectional view taken along the line X-X in FIG. 9.

The diaper 510a depicted in FIGS. 8 and 9 has the chassis 11 comprising a pair of side edges 15a of the front waist region 12 opposed to each other in the width direction W, a pair of side edges 15b of the rear waist region 13 opposed to each other in the width direction W and a pair of side edges 15c of the crotch region 14 opposed to each other in the width direction W. The chassis 11 is folded back along a center line D bisecting a length E of the chassis 11 with the inner sheet 11a inside and the respective pairs of side edges 15a, 15b put flat together are bonded one to another at bonding spots 51 arranged intermittently in a vertical direction as viewed in FIG. 7 to obtain the pants-type diaper 510 of FIG. 7.

As shown in FIG. 7, the diaper 510 is formed with a waist-hole 34 and a pair of leg-holes 35. The front and rear ends 12a, 14a are respectively provided with the waist elastic members 20 each comprising a plurality of rubber threads. Each of the waist elastic members 20 is sandwiched between the inner sheet 11a and the outer sheet 11b and bonded in a circumferentially stretched state to at least one of these sheets 11a, 11b. A peripheral edge defining each of the leg-holes 35 is provided with the leg elastic member 21 sandwiched between the inner sheet 11a and the outer sheet 11b and bonded in a stretched state to at least one of these sheets 11a, 11b. In the diaper 510, the front and rear waist regions 12, 13 of the chassis 11 are provided with auxiliary waist elastic members 36, each comprising a plurality of rubber threads, spaced one from another in the vertical direction and bonded in a circumferentially stretched state to the chassis 11. Such auxiliary waist elastic members 36 may be attached, if desired, also to the crotch region 14 in its zone defined below the respective pairs of side edges 15a, 15b. The outer sheet 11b constituting the chassis 11 is shaped to be longer than the outer sheet 11b in FIG. 1 in the length direction and the surplus end portions 11c are folded back along the front and rear ends 12a, 14a of the front and rear waist regions 12, 14, respectively, onto the inner side of the chassis 11 and bonded to the inner sheet 11a with an adhesive or sealing technique (See FIGS. 8 and 9). The outer sheet 11b is formed from a nonwoven fabric made of thermoplastic synthetic fibers and cooperates with a liquid-impervious or liquid-resistant leak-barrier film made of a thermoplastic synthetic resin which is larger than the absorbent 16 and placed on a portion of the outer sheet 11b overlying the absorbent 16 to function as a liquid-impervious sheet defining the outer surface of the chassis 11. On the inner surface of this chassis 11, the crotch region 14 or, in addition to the crotch region 14, zones of the front and rear waist regions in the vicinity of the crotch region 14 each being formed from the inner sheet 11a are liquid-pervious while zones formed from the surplus end portions 11c of the outer sheet 11b folded back onto the inner sheet 11a are liquid-impervious or liquid-resistant or liquid-pervious.

Referring to FIGS. 9 and 10, the absorbent 16 in the diaper 510 is formed on its zone opposed to the opening 26 of the spacer sheet 17 with a depression 52 which is devoid of the absorptive material. An inner surface of this depression 52 is defined by a semi-rigid sheet 37. The semi-rigid sheet 37 not only defines a bottom of the depression 52 but also covers a peripheral wall 53 of the depression 52. Around the depression 52, the semi-rigid sheet 37 is placed upon and bonded to the inner sheet 11a. The semi-rigid sheet 37 may be formed, for example, from a nonwoven fabric, a tissue paper or a thermoplastic synthetic resin film and preferably has a rigidity corresponding to or higher than the flexural rigidity of the absorbent 16. The depression 52 cooperates with the spacer sheet 17 to form the space 31 adapted to receive feces. In the chassis 11 containing the absorbent 16 formed with the depression 52, the inner surface of the depression 52 is formed from the semi-rigid sheet 37 and thereby it is unlikely that the crotch region 14 which becomes bulky outward as the diaper 510 is put on the wearer's body with the width of the crotch region 14 being reduced and folded in two in the width direction might be easily deformed during use of the diaper 510. The crotch region 14 is maintained bulky in this manner and consequently the spacer sheet 17 is largely spaced from the semi-rigid sheet 37 so as to form the correspondingly deeper space 31. Such space 31 not only improves its capacity to receive feces but also eliminates an anxiety that feces might flow back from the space 31. Use of the semi-rigid sheet 37 functioning in this manner allows the depression 52 to be replaced by water absorptive materials in the absorbent 16 locally compressed in the thickness direction. Preferably, the compressed water absorptive materials contains few or none of the super-absorbent polymer particles because the water absorptive material containing a significant amount of the super-absorbent polymer particles would be swollen as a result of water absorption and shallow the space 31.

The spacer sheet 17 of the diaper 510 is similar to the space sheet 17 in FIG. 4 except that the rear end zone 17b is spaced from the end 14b of the folded back end portion 11c of the outer sheet 11b so as to expose the inner sheet 11a between these rear end zone 17b and the folded back end portion 11c while the side edge zones 17c are spaced from the fixed sections 22b of the respective barrier cuffs 22 in the width direction W so as to expose the inner sheet 11a between these fixed sections 22b. The spacer sheet 17 arranged in this manner ensures that, even if loose passage flows on the spacer sheet 17 without being received by the opening 26, moisture content of this loose passage can be absorbed by the exposed zones of the inner sheet 11a around the spacer sheet 17.

In the diaper 510, the presence of the auxiliary waist elastic members 36 improves fitness of the front and rear waist regions 12, 13 with respect to the wearer's skin. It should be noted here that the middle zones of the front and rear waist regions 12, 13 as viewed in the width direction W occupied by the absorbent 16 hardly contract due to rigidity of the absorbent 16 and contractible zones of the front and rear waist regions 12, 13 are limited to the respective pairs of side edge zones in which the absorbent 16 is absent. Consequentially, the segment of the opening 26 lying in the rear waist region 13 and in the vicinity thereof is not significantly deformed under the effect of the auxiliary elastic members 36. At the same time, these auxiliary elastic members 36 assures a good fit of the diaper 510 with respect to the wearer's waist so that the position of the opening 26 relative to the wearer's body scarcely depends on movement and/or posture of the wearer and feces smoothly flow through the opening 26. In order to prevent the opening 26 from being deformed in the vicinity of the rear waist region 13, it is also possible to make a zone of the absorbent 16 across which the auxiliary elastic members 36 extend as well as the zone in the vicinity thereof relatively high. Alternatively, the auxiliary elastic members 36 may be cut in the middle zone of the chassis 11 as viewed in the width direction W or heat treated to eliminate the elasticity of the auxiliary elastic members 36 in these zones. In this way, deformation of the opening 26 otherwise possibly occurring in the vicinity of the rear waist region 13 can be prevented while stretch and contraction of the auxiliary elastic members 36 may be allowed for in the side edge sections of the rear waist region 13 of the chassis 11. Alternatively, the middle zone may be devoid of the auxiliary elastic members 36 and the side edge sections of the front waist region 12 or the rear waist region 13 may be provided with the auxiliary elastic members 36 to control the shape of the opening 26 primarily under the effect of the spacer elastic members 27. The diaper 510 implemented in the manner as has been described above ensures that the peripheral edge of the opening 26 is kept in close contact with the wearer's skin and thereby feces trapping capacity of the space 31 is improved while an apprehension of feces leak can be alleviated.

Figure 11:
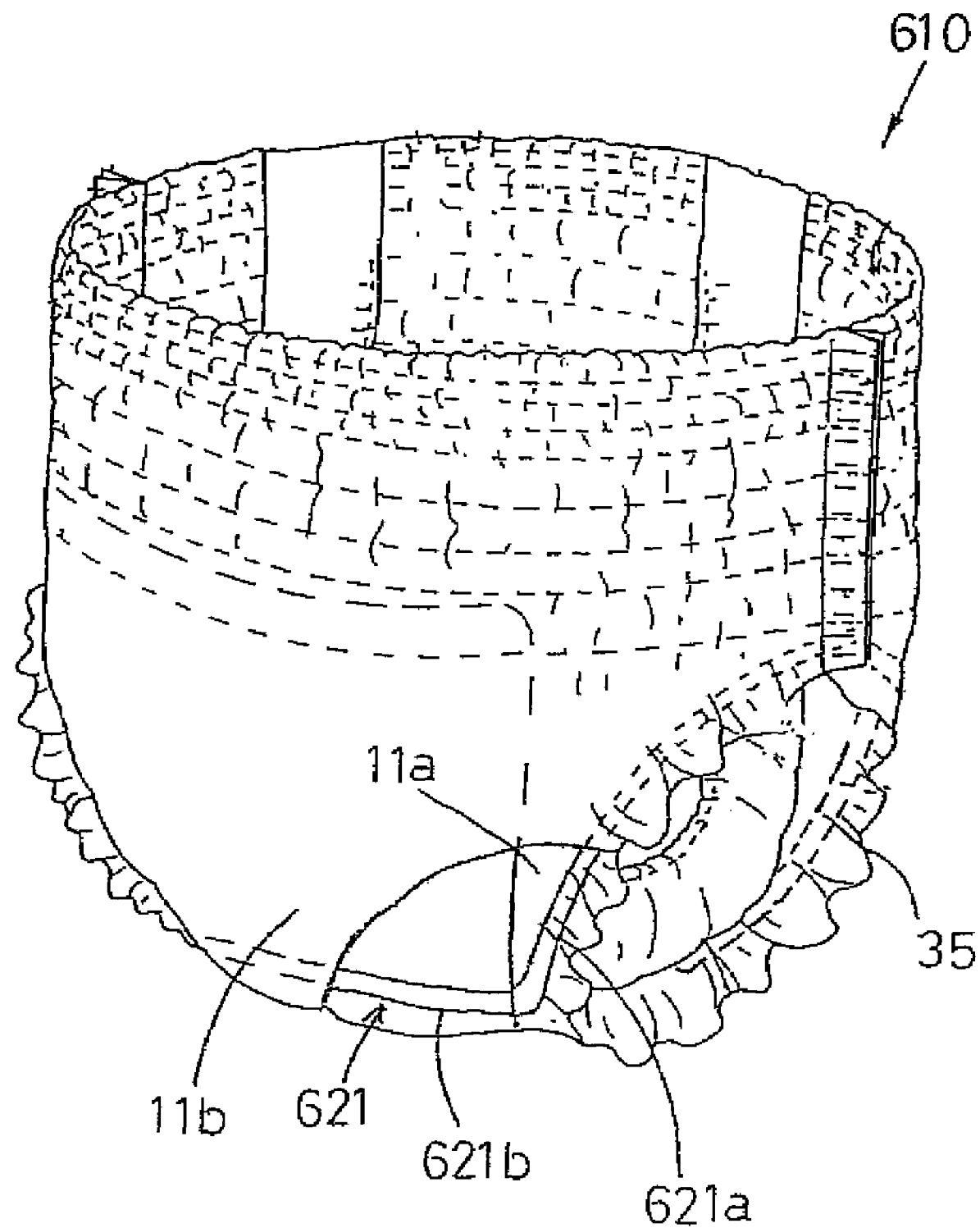
FIG. 11 is a partially cutaway perspective view depicting the pants-type diaper according to still another preferred embodiment of the present invention.

FIG. 11 is a partially cutaway perspective view depicting a pants-type diaper 610 according to still another preferred embodiment of the present invention. The diaper 610 is similar to the diaper 510 of FIG. 7 except that the leg elastic members 21 in FIG. 7 are replaced by leg elastic members 621 exploited in a manner as will be described. The leg elastic members 621 respectively comprise segments 621*a* extending around the leg-holes 35 so as to make substantially full circles and segments 621*b* extending across the crotch region 14. The leg elastic members 621 are attached in a stretched state to the diaper 610 and the segments 621*b* extending across the crotch region 14 function to reduce the width of the crotch region 14. The spacer elastic members 27 easily contract under the effect of the segments 621*b* and describe an X-shape as shown in FIG. 9. This X-shaped cross point comes in contact with the wearer's skin immediately in front of the anus.

In the diaper according to the present invention, the spacer sheet 17, 217, 317 attached to the liquid-pervious inner sheet 11*a* defining the inner surface of the diaper is formed from a relatively small sheet strip prepared separately of the inner sheet 11*a*. The spacer sheet 17, 217, 317 is adapted to come in close contact with the wearer's skin exclusively around the anus and formed with the opening 26 adapted to come in alignment with the anus as the diaper is put on the wearer's body so that feces can be reliably guided through the opening 26. The spacer sheet 17, 217, 317 is provided with the spacer elastic members 27 which function to space the spacer sheet 17, 217, 317 from the inner sheet 11*a* and thereby to form the space 31 and simultaneously function to taper the front segment 26*a* of the opening 26 forward. The front segment 26*a* tapered forward in this manner is formed along the peripheral edge thereof with a plurality of gathers. Such spacer sheet 17, 217, 317 is not directly affected by stretch and/or contraction of the elastic members located far apart from the opening 26 and therefore the shape of the opening 26 is scarcely affected by the elastic members other than the spacer elastic members 27. The spacer elastic members 27 extend neither to the front waist region 12 beyond the crotch region 14 nor to the rear end 14*a* of the rear waist region 13. In contrast to the case in which the spacer elastic members 27 extend to regions far apart from the opening 26, the position of the spacer sheet 17 relative to the wearer's body as well as the shape of the opening 26 scarcely depends on movement of the wearer's body and, in addition, it is ensured that the front segment 26*a* of the opening 26 and the zone in the vicinity thereof reliably come in contact with the wearer's skin immediately in front of the anus.

The present invention makes it possible to produce the disposable diaper free from anxiety that the wearer's skin might be soiled with feces.

The entire discloses of Japanese Patent application No. 2005-321609 filed on Nov. 4, 2005 including specification, drawings and abstract are herein incorporated by reference in its entirety.

What is claimed is:

1. A disposable diaper comprising:
a chassis having a length direction, a width direction orthogonal to said length direction, front and rear sides, a front waist region defined on said front side, a rear waist region defined on said rear side and a crotch region interposed in the length direction between said two waist regions, said regions respectively comprising an inner sheet adapted to come in contact with a wearer's skin and an outer sheet lying on the opposite side of said inner sheet and adapted to face away from the wearer;
an absorbent core interposed between said inner and outer sheets and bonded to said inner sheet;
a spacer sheet above said inner sheet and adapted to prevent feces discharged onto said inner sheet from coming in contact with said wearer's skin;
wherein said spacer sheet comprises:
a front end zone extending in the length direction toward said front side;
a rear end zone extending in the length direction toward said rear side;
an intermediate zone extending between said front and rear end zones, each of said zones having opposite side edges extending in said length direction at least one of said front and rear zones being at least partially fixed directly to said inner sheet while at least a middle spot of said intermediate zone being free of direct attachment to said inner sheet;
an opening provided in the middle spot of said intermediate zone, and adapted to guide said discharged feces therethrough toward said inner sheet, said intermediate zone around the opening being adapted to be put in contact with a vicinity of said wearer's anus, and
elastic members attached in a stretched state to said spacer sheet in a vicinity of side edges of said opening to extend in the length direction toward said front side so as to converge toward a center line extending in the length direction and bisecting a width of said diaper;
wherein the spacer sheet is free of elastic members along a rear edge of the opening.

2. The diaper defined by claim 1, wherein said elastic members provided in the vicinity of said side edges of said opening in a flatly developed state extend in said length direction substantially in parallel to each other.

3. The diaper defined by claim 1, wherein said elastic members provided in the vicinity of said side edges extend toward said front side so as to converge toward said center line and further extend to intersect with each other on said center line.

4. The diaper defined by claim 3, wherein said elastic members provided in the vicinity of said side edges extend toward said front side so as to intersect on said center line and further extend toward said front side so as to be spaced from each other.

5. The diaper defined by claim 1, wherein said elastic members, in a slackened state, extend toward said front side along said side edges and then extend further forward substantially linearly toward said center line.

6. The diaper defined by claim 3, wherein said elastic members provided in the vicinity of said side edges extend toward said front side so as to intersect with each other on said center line and further extend forward to where said front end zone of said spacer sheet is directly fixed to said inner sheet.

7. The diaper defined by claim 1, wherein said rear waist region of said chassis is provided along both sides thereof opposed to each other in said width direction with elastically stretchable/contractible zones, respectively, between which said rear end zone of said spacer sheet is laid on and fixed to said inner sheet in its region overlying said absorbent.

8. The diaper defined by claim 1, wherein said diaper is of a pants-type in which said front and rear waist regions in said chassis are bonded together along opposite side edges thereof.

9. The diaper defined by claim 1, wherein said elastic members contractibly extend in said width direction in said crotch region of said diaper.

10. The diaper defined by claim 1, wherein a width of said opening is gradually reduced in the length direction toward said front end zone of said spacer sheet.

11. The diaper defined by claim 1, wherein said spacer sheet extends toward the front waist region in the length direction and terminates before reaching the front waist region.

12. The diaper defined by claim 1, wherein said spacer sheet further comprises a notch located on said front end zone so that the inner sheet is partially exposed to receive the feces.

13. The diaper defined by claim 12, wherein said elastic members attached to the spacer sheet intersect between a front edge of the opening and a peripheral edge of said notch and further extend along the peripheral edge of said notch toward the front waist region.

14. The diaper defined by claim 12, wherein said front end zone of the spacer sheet is free of bonding to the inner sheet along the peripheral edge of said notch.

15. The diaper defined by claim 1, wherein said elastic members provided in the vicinity of said side edges extend toward said front side so as to converge toward said center line without intersecting with each other.

16. The diaper defined by claim 1, wherein said absorbent core defines a zone comprising a depression opposed to the opening of the spacer sheet and free of absorbent material to define a space adapted to receive the feces.

17. The diaper defined by claim 1, further comprising a sheet defining a bottom of the depression and extending in the length direction to be placed upon and bonded to the inner sheet to separate the absorbent core from the space.

* * * * *

UNITED STATES PATENT AND TRADEMARK OFFICE
CERTIFICATE OF CORRECTION

PATENT NO. : 7,654,990 B2
APPLICATION NO. : 11/533516
DATED : February 2, 2010
INVENTOR(S) : Nakajima et al.

It is certified that error appears in the above-identified patent and that said Letters Patent is hereby corrected as shown below:

On the title page, the names of the inventors should read as follows:

Item (75) Inventors: Kaiyo Nakajima, Kagawa-ken (JP); Hironao Minato, Kagawa-ken (JP); Toshimitsu Baba, Kagawa-ken (JP); NaokoTakada, Kagawa-ken (JP); Kaori Furuya, Kagawa-ken (JP)

Signed and Sealed this

Thirteenth Day of July, 2010

David J. Kappos
*Director of the United States Patent and Trademark Office*